United States Patent [19]

Matsuda et al.

[11] Patent Number: 5,196,586
[45] Date of Patent: Mar. 23, 1993

[54] POLYDIPHENYLDIACETYLENES

[75] Inventors: Hiro Matsuda; Shuji Okada; Hachiro Nakanishi; Masao Kato; Minoru Ohsugi, all of Tsukuba; Shigeru Takaragi; Nanao Horiishi, both of Hiroshima, all of Japan

[73] Assignees: Toda Kogyo Corp., Hiroshima; The Agency of Industrial Science and Technology, Tokyo, both of Japan

[21] Appl. No.: 742,760

[22] Filed: Aug. 9, 1991

Related U.S. Application Data

[63] Continuation-in-part of Ser. No. 479,438, Feb. 9, 1990, abandoned.

[30] Foreign Application Priority Data

Feb. 16, 1989 [JP] Japan .................................. 1-37020

[51] Int. Cl.$^5$ ................... C07C 211/44; C07C 43/215
[52] U.S. Cl. .................................. 564/442; 568/645; 568/646; 568/647
[58] Field of Search ............... 568/647, 585, 645, 646; 564/442

[56] References Cited

FOREIGN PATENT DOCUMENTS 0243807 11/1987 European Pat. Off. .

OTHER PUBLICATIONS

*Chemical Abstracts*, vol. 101, No. 4, Jul. 84, p. 11, Abstract No. 24111s (Agency of Industrial Sciences & Technology).
*Chemtronics*, vol. 3, Dec. 1988, pp. 211–214 "Synthesis Polymerization ... Novel Conjugated, Unsymmetrical Diacetylenes".
*Mol. Cryst. Liq. Cryst.*, 1988, vol. 160, pp. 241–151 "Synthesis and Solid-State Polymerization ... Nonlinear Optics".
*Macromolecules*, 1988, 21, p. 1238 Matsuda et al., "Synthesis and Solid State Polymerization of a New Diacetylene ... ".

*Primary Examiner*—Marianne M. Cintins
*Assistant Examiner*—Margaret J. Page
*Attorney, Agent, or Firm*—Nixon & Vanderhye

[57] ABSTRACT

Disclosed herein are polydiphenyldiacetylenes having the following repeating unit (III):

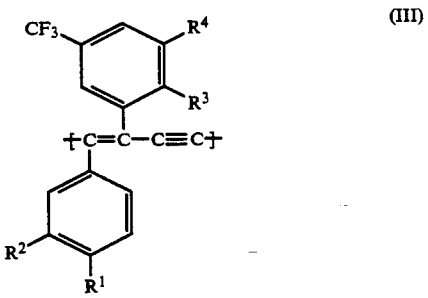

(III)

(wherein $R^1$ denotes a hydrogen atom or a methoxy group; $R^2$ denotes a hydrogen atom, a methoxy group or a methylamino group; $R^3$ denotes a hydrogen atom or a trifluoromethyl group; and $R^4$ denotes a hydrogen atom or a trifluoromethyl group; provided that $R^1$ is not a hydrogen atom when $R^2$ is hydrogen atom, and $R^3$ is not a hydrogen atom when $R^4$ is hydrogen atom).

4 Claims, No Drawings

POLYDIPHENYLDIACETYLENES

CROSS-REFERENCE TO RELATED APPLICATION

This application is a continuation-in-part of U.S. patent application, Ser. No. 479,438 filed on Feb. 9, 1990, now abandoned.

BACKGROUND OF THE INVENTION

The present invention relates to polydiphenyldiacetylenes and particularly, to polydiphenyldiacetylenes obtained by a solid-state polymerization. Such polydiphenyldiacetylenes according to the present invention are useful as functional materials such as non-linear optical materials, photosensitive materials, semiconductive polymer crystals and the like because they are obtained by solid-state polymerization of diphenyldiacetylenes.

In recent years, researches have been actively made on diacetylene compounds serving as monomers used for forming non-linear optical materials, photosensitive materials, semiconductive polymer crystals and the like.

For forming non-linear optical materials, photosensitive materials and semiconductive polymer crystals, polydiacetylenes obtained by a solid-state polymerization are used. It has been also already known that, in order to improve the non-linear optical effect of non-linear optical materials, the diacetylene monomers used must have an unsymmetrical structure and exhibit a large electronic effect owing to the conjugation bond between the main chain and the side chains.

It is generally known that some of diacetylene compounds represented by the following formula (I) have solid-state polymerizability.

$$R_a-C\equiv C-C\equiv C-R_b \quad (I)$$

There is now a strong demand for monomers having solid-state polymerizability, an unsymmetrical structure and substituents which are conjugated with the diacetylene triple bonds. However, as each the above-described known diacetylene compounds having solid-state polymerizability has the same substituent at both ends of the diacetylene part, i.e., $R_a=R_b$ in the formula (I), to form a symmetric molecule, a charge-transfer effect cannot be at all expected.

In addition, most of such diacetylene compounds have a structure in which the conjugation bond between the substituents and the diacetylene part is cut off. In this way, polymers in each of which the conjugation bond between the main chain and the side chains is cut off, exhibit substantially no electronic effect of the substituents $R_a$ and $R_b$, and any substituents in the polymers have the tendency to exhibit similar properties.

On the other hand, since diacetylene compounds represented by the formula (I), having as the substituents $R_a$ and $R_b$ aromatic groups have conjugation bond between the triple bonds and the substituents, it is expected that the crystalline polymers formed have excellent electronic properties. However, most of such diacetylene compounds exhibit no solid-state polymerizability.

Some diphenyldiacetylene compounds each of which has two phenyl groups each having acetylamino groups at the ortho and meta positions or two phenyl groups each having trifluoromethyl groups at the 2- and 4-position, 2- and 5-position or 3- and 5-position, have solid-state polymerizability. However, each of these compounds has a symmetric structure in the molecule and thus exhibits no charge-transfer effect.

As described above, diacetylene monomers each of which has solid-state polymerizability, an unsymmetrical structure and aromatic groups as substituents which are conjugated with the diacetylene triple bonds, and each of which thus exhibits a large electronic effect, has been desired as the starting material of the non-linear optical materials.

European Patent 0 243 807 A discloses a process for production of a polydiacetylenic composition which comprises polymerizing a diacetylene monomer corresponding to the formula:

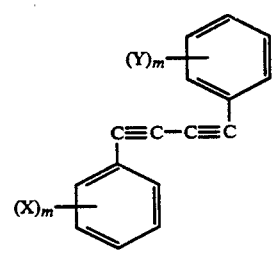

(where X is an electron-donating substituent, Y is an electron-withdrawing substituent, and m is the integer one or two) and a polymeric composition which is characterized by the recurring monomeric unit:

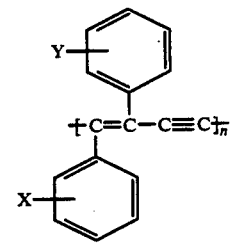

(where X is an electron-donating substituent; Y is an electron-withdrawing substituent; and n is an integer of at least 3). Further, as a concrete embodiment of the polymeric composition, European Patent 0 243 807 A discloses a preparation of polymer:

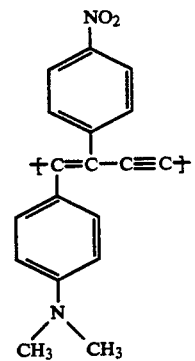

obtained by casting a sample of 1-(4-N,N-dimethylaminophenyl-4-(4-nitrophenyl)-1,4-butadiyne in tetrahydrofuran on an optical glass substrate, evaporating the solvent to form a coating on the substrate, an heating the coated glass substrate at 250° C. for ten minutes to produce a transparent continuous film of polymer on the glass surface. This polymerization is a liquid-state polymerization.

However, it is not said that the non-linear susceptibility of such polydiacetylenic composition is sufficient. Accordingly, it is strongly demanded to provide polydiphenyldiacetylenes having a high non-linear susceptibility, prepared by the solid-state polymerization of the corresponding diphenyldiacetylene monomers.

As a result of the inventors' studies for satisfying the above-mentioned demands, it has been found that by solid-state polymerizing diphenyldiacetylene derivatives represented by the following formula (II) having an unsymmetrical structure and exhibiting a large electronic effect.

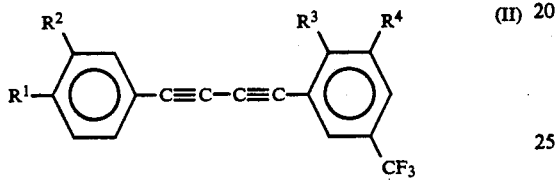

(wherein R$^1$ denotes a hydrogen atom or a methoxy group; R$^2$ denotes a hydrogen atom, a methoxy group or a methylamino group; R$^3$ denotes a hydrogen atom or a trifluoromethyl group; and R$^4$ denotes a hydrogen atom or a trifluoromethyl group; provided that R$^1$ is not a hydrogen atom when R$^2$ is a hydrogen atom, and R$^3$ is not a hydrogen atom when R$^4$ is a hydrogen atom), the obtained polydiphenyldiacetylenes are a single crystal polymer having a high non-linear susceptibility and a substantially 100% crystallinity in which the conjugated main chain is linearly oriented and which is the same size and shape as a crystal of the diphenyldiacetylene monomers and substantially free from faults.

The present invention has been achieved on the basis of this finding.

SUMMARY OF THE INVENTION

In a first aspect of the present invention, there is provided polydiphenyldiacetylenes having a single-crystal form of a substantially 100% crystallinity, a non-linear susceptibility of not less than $1 \times 10^{-10}$ esu and a repeating monomeric unit(III):

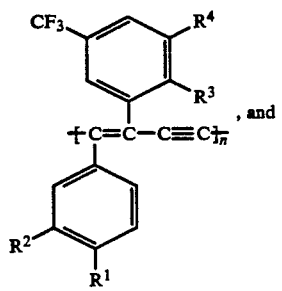

produced by solid-state polymerizing a diphenyldiacetylene derivative represented by the following formula (II):

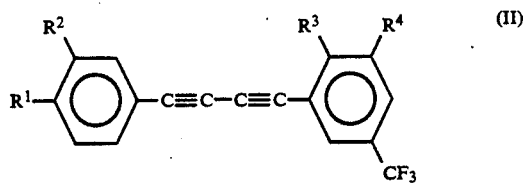

(wherein R$^1$ denotes a hydrogen atom or a methoxy group; R$^2$ denotes a hydrogen atom, a methoxy group or a methylamino group; R$^3$ denotes a hydrogen atom or a trifluoromethyl group; R$^4$ denotes hydrogen atom or a trifluoromethyl group; and n is an integer of at least 50 provided that R$^1$ is not a hydrogen atom when R$^2$ is hydrogen atom, and R$^3$ is not a hydrogen atom when R$^4$ is hydrogen atom).

DETAILED DESCRIPTION OF THE INVENTION

As the starting material, diphenyldiacetylene derivatives represented by the formula (II) of the present invention are a functional material, and examples of the derivatives include the following compounds.

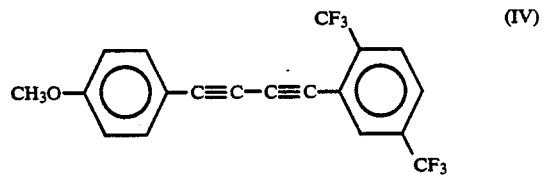

(Compound No. 1)

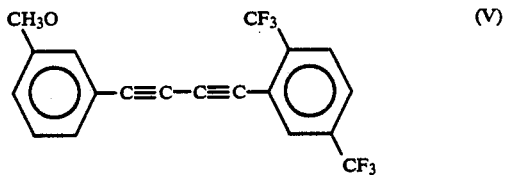

(Compound No. 2)

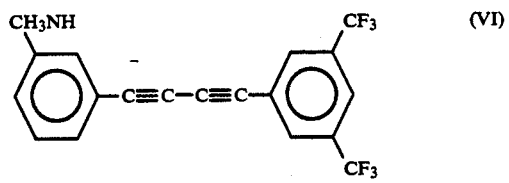

(Compound No. 3)

Each of the diphenyldiacetylene derivatives represented by the formula (II) enables to produce non-linear optical materials, photosensitive materials and semiconductive polymer crystals owing to the solid-state polymerizability, and exhibits a large non-linear optical effect owing to the large electronic effect caused by the unsymmetrical structure and the aromatic substituents which are conjugated with the diacetylene triple bonds.

Each of the diphenyldiacetylene derivatives represented by the formula (II) has trifluoromethyl groups (—CF$_3$) serving as electron attractive groups and methoxy groups or N-methylamino groups serving as electron donative groups and is a compound which is significantly polarized in molecule. Therefore, a large non-linear optical effect can be thus expected, and the derivatives are significantly effective for use as non-linear materials.

The process for producing diphenyldiacetylene derivatives represented by the formula (II) is set forth below.

Ethynylbenzene derivatives represented by the following formula (VII):

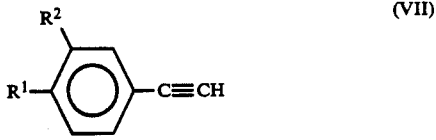

(wherein $R^1$ and $R^2$ each denote the same as that described above) and 1-bromo-3-hydroxy-3-methyl-1-butyne represented by the following formula (VIII):

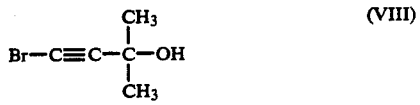

are subjected to unsymmetrical coupling reaction. The resultant diacetylene derivatives represented by the following formula (IX):

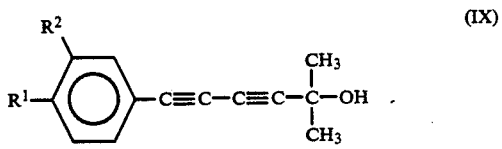

(wherein $R^1$ and $R^2$ each denote the same as described above) is deacetonated in the presence of a basic catalyst The resultant phenylbutadiyne derivatives represented by the following formula (X):

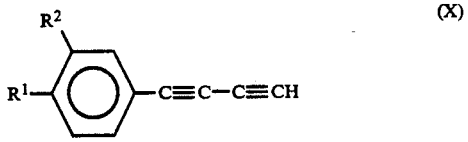

(wherein $R^1$ and $R^2$ each denote the same as described above) and bis(trifluoromethyl) iodobenzene represented by the following formula (XI):

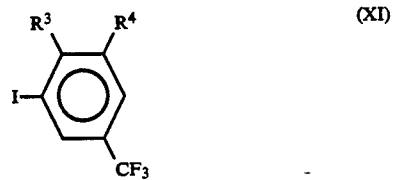

(wherein $R^3$ and $R^4$ each denote the same as described above) are subjected to coupling reaction in the presence of a palladium catalyst to form the diphenyldiacetylene derivatives represented by the formula (II).

Although the unsymmetrical coupling reaction of acetylene derivatives can be carried out under various reaction conditions, the catalytic function of a copper salt is required in any cases. Specifically, the unsymmetrical coupling reaction is carried out by adding an amine and copper (I) chloride to a solution of an ethynylbenzene derivative (ethynylanisole) and then slowly adding 1-bromo-3-hydroxy-3-methyl-1-butyne to the reaction mixture under stirring.

A polar solvent such as methanol, ethanol, tetrahydrofuran, dimethylformamide, dimethylacetamide or the like is preferably used as a solvent. An aqueous ethylamine solution is generally used as the amine, and isopropylamine or the like can be used when the reaction is carried out in a hydrophobic system. The copper (I) chloride is used in an amount within the range of from 1 to 50 mol % based on the amount of ethynylaniline used.

This reaction is performed at 0° to 50° C. in an atmosphere of inert gas such as argon or nitrogen gas. In some cases, the reaction is performed for several hours to two days while an appropriate amount of hydroxylamine hydrochloride being added under stirring for preventing oxidation of copper (I) ions.

After the reaction has been completed, the solvent is evaporated from the reaction mixture, and the residue is neutralized and diluted by an aqueous solution of diluted hydrochloric acid and then subjected to extraction with a solvent such as ether, benzene or the like. The solution obtained is dehydrated by adding a drying agent such as sodium sulfate, magnesium sulfate or the like thereto, and the drying agent and the solvent are then removed. The residue is purified by silica-gel column chromatography to obtain a diacetylene derivative represented by the formula (IX).

The thus-obtained diacetylene derivative represented by the formula (IX) is then dissolved in benzene and refluxed while being heated for 30 min. to 1 hour in the presence of potassium hydroxide. After the reaction has been completed, the reaction mixture is filtered, and the solvent is then evaporated. The residure is then purified by silica-gel column chromatography to obtain a phenylbutadiyne derivative represented by the formula (X).

Coupling reaction between the thus-formed phenylbutadiyne derivative and an aryl iodide represented by the formula (XI) can be under various reaction conditions and in any cases, the catalytic function of palladium (0) is required.

Specifically, the reaction is progressed by dissolving bis(trifluoromethyl) iodobenzene and the phenylbutadiyne derivative represented by the formula (X) in the amine solvent and adding bis(triphenylphosphine) palladium (II) chloride to the resultant solution.

Triethylamine, diethylamine and the like can be used as the solvent and, when the aryl iodide represented by the formula (XI) or the phenylbutadiyne derivative represented by the formula (X) is slightly soluble in the solvent, a solvent mixture of benzene or toluene and triethylamine or diethylamine can be used.

In the coupling reaction of the diphenyldiacetylene derivative, the reaction is carried out in an atmosphere of inert gas such as argon or nitrogen gas, and a reaction initiator such as copper (I) iodide or copper (I) chloride may be added thereto.

After the reaction has been completed, the precipitates produced are filtered off from the reaction mixture, and the filtrate is concentrated, neutralized and diluted with diluted hydrochloric acid, and then subjected to extraction with a solvent such as ether, benzene or the like. The organic layer is dehydrated by a drying agent such as sodium sulfate or magnesium sulfate, and the solvent is then removed. The residue is then purified by silica-gel column chromatography to obtain a diphenyldiacetylene derivative represented by the formula (II).

The solid-state polymerization of the diphenyldiacetylene derivative represented by the formula (II) is conducted by exposing to ultraviolet radiation or γ-ray, or heating to a temperature sufficiently high for exciting the diphenyldicetylene monomer.

The ultraviolet radiation treatment in the range of 1 to 200 W for 1 to 100 min. and γ-ray treatment in the range of 1 to 350M rad are preferred. The heat treatment at a temperature of less than the melting point of the diphenyldiacetylene monomer for 48 to 120 hrs, is preferred.

The polydiphenyldiacetylenes according to the present invention are ones obtained by polymerizing the diphenyldiacetylene monomers at the conversion of substantially 100% and are insoluble to organic solvents such as benzene, acetone, chloroform, cyclohexanone, dimethylformamide and tetrahydrofuran.

A film of the polydiphenyldiacetylenes according to the present invention can be prepared by forming a thin substrate of the diphenyldiacetylene monomer in a highly ordered state, and then solid-state polymerizing the monomer on the substrate to form a corresponding thin polymeric film.

From X-ray diffraction pattarn, the polydiphenyldiacetylenes according to the present invention have a singlecrystal form of a substantially 100% crystallinity (i.e., 95 to 100% crystallinity, preferably 98 to 100% crystallinity).

The polydiphenyldiacetylenes according to the present invention has a non-linear susceptibility of not less than $1 \times 10^{-10}$ esu, preferably not less than $3.5 \times 10^{-10}$ esu as determined by the method described on page 7 of Garito in "Non-linear Optical Properties of Organic and Polymeric Materials", ACS Symposium Series 233, American Chemical Society, Washington, D.C. 1983.

The polydiphenyldiacetylenes according to the present invention is useful as non-linear optical materials, photosensitive materials and semiconductive polymer materials.

The present invention will be described in detail below with reference to examples and a reference example, but the present invention is not limited to the examples.

EXAMPLE 1

100 mg of copper (I) chloride was dissolved in a mixture of 20 ml of isopropylamine and 20 ml of methanol in an atmoshpere of argon, and 1320 mg of 4-ethynylanisole were added to the resultant solution, followed by stirring at room temperature for 10 minutes. 2700 mg of 1-bromo-3-hydroxy-3-methyl-1-butyne were then dropwisely added to the solution over a time of about 3 hours, followed by stirring at room temperature fo 2 hours (If the solution is colored green owing to the production of copper (II) ion, an appropriate amount of hydroxilamine hydrochloride is added so as to reduce the copper (II) ion). The solvent was then evaporated from the reaction mixture, and the residue was neutralized and diluted by 1N hydrochloric acid, and then subjected to extraction with 50 ml of dichloromethane three times. The organic layer was dried over magnesium sulfate, and the solvent was then evaporated. The residue was then purified by silica-gel column chromatography using benzene as an eluent to obtain 1500 mg of 5-hydroxy-5-methyl-1-(4-methoxyphenyl)hexa-1,3-diyne.

1500 mg of the diacetylene compound obtained were then dissolved in 300 ml of benzene, and 600 mg of potassium hydroxide, which were finely ground, was then added to the reaction mixture, followed by reflux under heating for 30 minutes. After filtration, the solvent was evaporated, and the residue was then purified by silica-gel chromatrgaphy using hexane as an eluent to obtain 1150 mg of 1-(4-methoxyphenyl)-1,3-butadiyne. This compound was a slightly yellowish white crystal.

1100 mg of the 1-(4-methoxyphenyl)-1,3-butadiyne obtained and 2700 mg of 2,5-bis(trifluoromethyl) iodobenzene were then dissolved in 50 ml of triethylamine, and 50 mg of bis(triphenylphosphine)palladium (II) chloride and 14 mg of copper (I) chloride were then rapidly added to the reaction mixture. After the solution had been stirred at room temperature for 13 hours, 50 ml of benzene were added to the reaction mixture, and the precipitates produced were then filtered off. After the solvent had been evaporated, the residue was neutralized by 1N hydrochloric acid and subjected to extraction with 50 ml of benzene three times. The organic layer was dried over magnesium sulfate, and the solvent was then evaporated. The residue was purified by silica-gel column chromatography using hexane as an eluent to obtain 1600 mg of 1-(4-methoxyphenyl)-4-[2,5-bis(trifluoromethyl)phenyl]-1,3-butadiyne. This compound was a needle-like white crystal having a melting point of from 86° to 88° C.

Anal. Calc'd For ($C_{19}H_{10}F_6O$): C, 61.97%, H, 2.74%. Found: C, 61.68%, H, 2.98%.

A powder of the thus obtained 1-(4-methoxyphenyl)-4-[2,5-bis(trisfluoromethyl)phenyl]-1,3-butadiyne was loaded into a glass tube under vacuum and irradiated with ultraviolet radiation at the dose of 150 W for 20 min. so as to be solid-state polymerized. After the glass tube had been opened, the polymerization yield was determined from the weight of the polymer which was insoluble in benzene. The yields for all the samples were 100%.

The obtained polymer was insoluble to benzene, acetone chloroform, cyclohexanone, dimethylformamide and tetrahydrofuran. The non-linear susceptibility of the obtained polymer film was $2 \times 10^{-10}$ esu.

From the result of examination of X-ray diffraction pattern, the obtained polymer had a single crystal of 100% crystallinity.

EXAMPLE 2

50 mg of copper (I) chloride were dissolved in a mixture of 10 ml of isopropylamine and 15 ml of methanol in an atmosphere of argon, and 660 mg of 3-ethynylanisole were then added to the reaction mixture, followed by stirring at room temperature for 10 minutes. 1300 mg of 1-bromo-3-hydroxy-3-methyl-1-butyne were then dropwisely added to the solution over a time of about 2 hours, followed by stirring at room temperature for 2 hours. The solvent was then evaporated from the reaction mixture, and the residue was then neutralized and diluted by 1N hydrochloric acid, and subjected to extraction with dichloromethane three times. The organic layer was then dried over magnesium sulfate, and the solvent was then evaporated. The residue was then purified by silica-gel column chromatography using benzene as an eluent to obtain 800 mg of 5-hydroxy-5-methyl-1-(3-methoxyphenyl)hexane-1,3-diyne.

800 mg of the thus-obtained diacetylene compound were dissolved in 200 ml of benzene, and 300 mg of potassium hydroxide were added to the reaction mixture, followed by reflux under heating for 15 minutes. After filtration, the solvent was evaporated, and the residue was purified by silica-gel chromatography using as hexane as an eluent to obtain 430 mg of 1-(3-methoxyphenyl)-1,3-butadiyne.

430 mg of the thus-obtained 1-(3-methoxyphenyl)-1,3-butadiyne and 1200 mg of 2,5-bis(trifluoromethyl) iodobenzene were dissolved in 20 ml of triethylamine in an atmosphere of argon, and 21 mg of bis(triphenylphosphine) palladium (II) chloride and 6 mg of copper (I) chloride were rapidly added to the reaction mixture. After the solution had been stirring at room temperature for 13 hours, 30 ml of benzene were added thereto, and the precipitates produced were filtered off. After the solvent had been evaporated, the residue was neutralized by 1N hydrochloric acid and then subjected to extraction with 50 ml benzene three times. The organic layer was dried over magnesium sulfate, and the solvent was then evaporated. The residue was then purified by silica-gel column chromatography using hexane as an eluent to obtain 300 mg of 1-(3-methoxyphenyl)-4-[2,5-bis(trifluoromethyl)phenyl]-1,3-butadiyne. This compound was a slightly yellowish white crystal having a melting point of 37° C.

Anal. Calc'd For ($C_{19}H_{10}F_6O$): C, 61.97%, H, 2.74%. Found: C, 61.72%, H, 2.85%.

The thus obtained 1-(3-methoxyphenyl)-4-[2,5-bis(trifluoromethyl)phenyl]-1,3-butadiyne was loaded into a glass tube under vacuum and irradiated with cobalt-60 γ-rays at the dose of 300 MRAD so as to be solid-state polymerized. After the glass tube had been opened, the polymerization yield was determined from the weight of the polymer which was insoluble in benzene. The yields for all the samples were 100%.

The obtained polymer was insoluble to benzene, acetone, chloroform, cyclohexanone, dimethylformamide and tetrahydrofuran. The non-linear susceptibility of the obtained polymer film was $1 \times 10^{-10}$ esu.

From the result of examination of X-ray diffraction pattarn, the obtained polymer had a singlecrystal of 99% crystallinity.

EXAMPLE 3

100 mg of copper (I) chloride were dissolved in a mixture of 20 ml of isopropylamine and 10 ml of methanol in an atmosphere of argon, and 1350 mg of 3-ethynyl-N-methylaniline were then added to the reaction mixture, followed by stirring at room temperature for 10 minutes. 3300 mg of 1-bromo-3-hydroxy-3-methyl-1-butyne were then dropwisely added to the solution over a time of about 3 hours, followed by stirring at room temperature for 2 hours. After the solvent had been evaporated from the reaction mixture, the residue was neutralized and diluted by 1N hydrochloric acid and subjected to extraction with 50 ml of ether three times. The organic layer was dried over magnesium sulfate, and the solvent was then evaporated. The residue was then purified by silica-gel chromatography using benzene as an eluent to obtain 1600 mg of 5-hydroxy-5-methyl-1-[3-(N-methylamino)phenyl] hexa-1,3-diyne.

1600 mg of the thus-obtained diacetylene compound were then dissolved in 300 ml of benzene, and 450 mg of potassium hydroxide were then added to the reaction mixture, followed by reflux under heating for 1 hour. After filtration, the solvent was evaporated, and the residue was then purified by silica-gel column chromatography using benzene as an eluent to obtain 500 mg of 1-[3-(N-methylamino)phenyl]-1,3-butadiyne.

320 mg of the thus-obtained 1-[3-(N-methylamino)phenyl]-1,3-butadiyne and 700 mg of 3,5-bis(trifluoromethyl) iodobenzene were dissolved in 30 ml of trimethylamine in an atmosphere of argon, and 14 mg of bis(triphenylphosphine)palladium (II) chloride and 4 mg of copper (I) chloride were then rapidly added to the reaction mixture. After the solution had been stirred at room temperature for 13 hours, 50 ml of benzene were added thereto, and the solvent was then evaporated. The residue was neutralized by 1N hydrochloric acid and subjected to extraction with 50 ml of benzene three times. The organic layer was then dried over magnesium sulfate, and the solvent was evaporated. The residue was then purified by silica-gel chromatography using a mixture of hexane and benzene as an eluent to obtain 580 mg of 1-[3-(N-methylamino)phenyl]-4-[3,5-bis(trifluoromethyl)phenyl]-1,3-butadiyne. This compound was a yellowish green crystal having a melting point of from 75° to 76° C.

Anal. Calc'd For ($C_{19}H_{11}F_6N$): C, 62.13%; H, 3.02%; N, 3.81%. Found: C, 61.92%; H, 3.14%; N, 4.03%.

A powder sample of the obtained 1-[3-(N-methylamino)phenyl]-4-[3,5-bis(trifluoromethyl)phenyl]-1,3-butadiyne was loaded into a glass tube under vacuum and irradiated with cobalt-60 γ-rays at the dose of 300 MRAD so as to be solid-state polymerized. After the glass tube had been opened, the polymerization yield was determined from the weight of the polymer which was insoluble in benzene. The yields for all the samples were 100%.

The obtained polymer was insoluble to benzene, acetone, chloroform, cyclohexanone, dimethylformamide and tetrahydrofuran. The non-linear susceptibility of the polymer was $4 \times 10^{-10}$ esu.

From the result of examination of X-ray diffraction pattern, the obtained polymer had a singlecrystal of 100% crystallinity.

What is claimed is:

1. Polydiphenyldiacetylenes having a single crystal form of substantially 100% crystallinity, a non-linear susceptibility of not less than $1 \times 10^{-10}$ esu and a repeating monomeric unit (III):

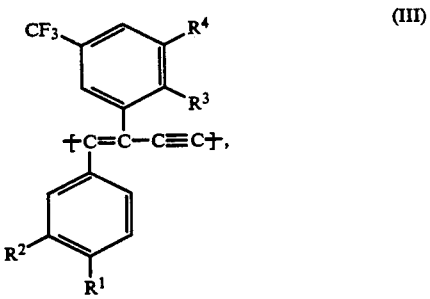

and produced by solid-state polymerizing a diphenyldiacetylene derivative represented by the following formula (II):

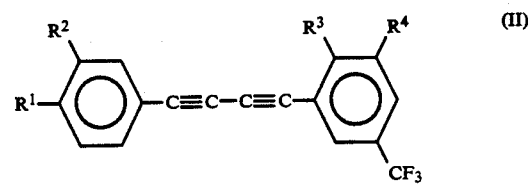

wherein $R^1$ denotes a hydrogen atom or a methoxy group; $R^2$ denotes a hydrogen atom, a methoxy group or a methylamino amino group; $R^3$ denotes a hydrogen atom or a trifluoromethyl group; and $R^4$ denotes a hydrogen atom or a trifluoromethyl group; provided that $R^1$ is not a hydrogen atom when $R^2$ is hydrogen atom, and $R^3$ is not a hydrogen atom when $R^4$ is hydrogen atom, wherein said solid-state polymerizing is conducted by exposing the diphenyldiacetylene derivative to ultraviolet radiation or $\gamma$-rays, or by heating to a temperature sufficiently high for exciting the diphenyldiacetylene derivative.

2. The polydiphenyldiacetylenes according to claim 1, wherein $R^1$ denotes a methoxy group; $R^2$ and $R^4$ each denote a hydrogen atom; and $R^3$ denotes a trifluoromethyl group.

3. The polydiphenyldiacetylenes according to claim 1, wherein $R^1$ and $R^4$ each denote a hydrogen atom; $R^2$ denotes a methoxy group; and $R^3$ denotes a trifluoromethyl group.

4. The polydiphenyldiacetylene derivative according to claim 1, wherein $R^1$ and $R^3$ each denote a hydrogen atom; $R^2$ denotes a methylamino group; and $R^4$ denotes a trifluoromethyl group.

* * * * *

UNITED STATES PATENT AND TRADEMARK OFFICE
CERTIFICATE OF CORRECTION

PATENT NO. : 5,196,586

DATED : March 23, 1993

INVENTOR(S) : MATSUDA et al

It is certified that error appears in the above-identified patent and that said Letters Patent is hereby corrected as shown below:

Column 11, line 3 (claim 1), "methylamino amino" should read

--methylamino--.

Signed and Sealed this

Eighteenth Day of January, 1994

*Attest:*

BRUCE LEHMAN

*Attesting Officer*  *Commissioner of Patents and Trademarks*